(12) United States Patent  (10) Patent No.: US 9,192,489 B2
Zamponi et al.  (45) Date of Patent: Nov. 24, 2015

(54) METHOD FOR PRODUCING A MEDICAL DEVICE

(75) Inventors: Christiane Zamponi, Kiel (DE); Rodrigo Lima De Miranda, Kiel (DE)

(73) Assignee: ACANDIS GMBH & CO. KG, Pfinztal (DE)

( * ) Notice: Subject to any disclaimer, the term of this patent is extended or adjusted under 35 U.S.C. 154(b) by 605 days.

(21) Appl. No.: 13/695,136

(22) PCT Filed: Apr. 28, 2011

(86) PCT No.: PCT/EP2011/002137
§ 371 (c)(1),
(2), (4) Date: Feb. 1, 2013

(87) PCT Pub. No.: WO2011/134662
PCT Pub. Date: Nov. 3, 2011

(65) Prior Publication Data
US 2013/0199713 A1  Aug. 8, 2013

(30) Foreign Application Priority Data
Apr. 28, 2010 (DE) .......................... 10 2010 018 541

(51) Int. Cl.
| | |
|---|---|
| *B29C 65/48* | (2006.01) |
| *B29C 65/52* | (2006.01) |
| *B32B 37/10* | (2006.01) |
| *B32B 37/12* | (2006.01) |
| *B32B 38/10* | (2006.01) |

(Continued)

(52) U.S. Cl.
CPC ............. *A61F 2/82* (2013.01); *A61F 2240/001* (2013.01)

(58) Field of Classification Search
USPC .......................................... 156/247, 249, 278
See application file for complete search history.

(56) References Cited

U.S. PATENT DOCUMENTS

| | | | | |
|---|---|---|---|---|
| 5,891,191 | A * | 4/1999 | Stinson | 623/1.2 |
| 6,682,473 | B1 * | 1/2004 | Matsuura et al. | 600/29 |
| 6,976,950 | B2 * | 12/2005 | Connors et al. | 600/29 |

(Continued)

FOREIGN PATENT DOCUMENTS

| | | |
|---|---|---|
| DE | 102006029831 | 1/2008 |
| DE | 102006039840 | 3/2008 |

(Continued)

OTHER PUBLICATIONS

International Search Report for PCT.2011/002137, English translation attached to original, Both completed by the European Patent Office on Oct. 5, 2011, All together 5 Pages.

*Primary Examiner* — Sing P Chan
(74) *Attorney, Agent, or Firm* — Brooks Kushman P.C.

(57) ABSTRACT

A method for producing a medical device with a lattice structure, connected at least in some areas to a cover. The lattice structure is arranged on a substrate via the side to be connected to the cover, the lattice structure has the side arranged on the substrate pressed at least partially into the substrate, the lattice structure is coated with a first layer of a sacrificial material. At least some of the interstices of the lattice structure are covered by the first layer, and the first layer with the lattice structure on the side to be connected to the cover forms a substantially closed surface, the substrate is removed, making the side of the lattice structure accessible for connection to the cover. A second layer for forming the cover is applied to the side of the lattice structure previously pressed into the substrate, and the sacrificial material is removed.

16 Claims, 4 Drawing Sheets

(51) Int. Cl.
*B32B 43/00* (2006.01)
*A61F 2/82* (2013.01)

(56) References Cited

U.S. PATENT DOCUMENTS

| | | | |
|---|---|---|---|
| 6,976,951 B2* | 12/2005 | Connors et al. | 600/29 |
| 6,988,983 B2* | 1/2006 | Connors et al. | 600/29 |
| 7,074,178 B2* | 7/2006 | Connors et al. | 600/29 |
| 7,374,532 B2* | 5/2008 | Connors et al. | 600/29 |
| 7,470,228 B2* | 12/2008 | Connors et al. | 600/30 |
| 7,484,510 B2* | 2/2009 | Connors et al. | 128/897 |
| 7,691,051 B2* | 4/2010 | Connors et al. | 600/29 |
| 7,727,275 B2* | 6/2010 | Betts et al. | 623/1.46 |
| 7,740,474 B2* | 6/2010 | Scheibel et al. | 432/261 |
| 7,771,463 B2* | 8/2010 | Ton et al. | 623/1.11 |
| 7,883,399 B2* | 2/2011 | Tallberg et al. | 452/21 |
| 8,003,157 B2* | 8/2011 | Andreacchi et al. | 427/2.24 |
| 8,025,064 B2* | 9/2011 | Connors et al. | 128/897 |
| 8,133,269 B2* | 3/2012 | Flechsenhar et al. | 623/1.46 |
| 8,298,132 B2* | 10/2012 | Connors et al. | 600/30 |
| 8,308,928 B2 | 11/2012 | Quandt et al. | |
| 8,313,600 B2* | 11/2012 | Wilson et al. | 156/175 |
| 8,318,297 B2* | 11/2012 | Tian et al. | 428/304.4 |
| 8,444,900 B2* | 5/2013 | Wilson et al. | 264/258 |
| 8,840,736 B2* | 9/2014 | Harder et al. | 148/420 |
| 8,852,267 B2* | 10/2014 | Cattaneo | 623/1.24 |
| 8,858,460 B2* | 10/2014 | Connors et al. | 600/561 |
| 8,888,842 B2* | 11/2014 | Gulcher | 623/1.46 |
| 9,050,391 B2* | 6/2015 | Schlottig et al. | 1/1 |
| 2003/0229263 A1* | 12/2003 | Connors et al. | 600/29 |
| 2003/0229264 A1* | 12/2003 | Connors et al. | 600/29 |
| 2003/0235561 A1* | 12/2003 | Vandenburgh et al. | 424/93.21 |
| 2003/0236442 A1* | 12/2003 | Connors et al. | 600/29 |
| 2004/0098108 A1* | 5/2004 | Harder et al. | 623/1.15 |
| 2004/0138520 A1* | 7/2004 | Connors et al. | 600/29 |
| 2004/0254419 A1* | 12/2004 | Wang et al. | 600/8 |
| 2005/0025797 A1* | 2/2005 | Wang et al. | 424/422 |
| 2005/0038505 A1* | 2/2005 | Shulze et al. | 623/1.42 |
| 2005/0079132 A1* | 4/2005 | Wang et al. | 424/1.11 |
| 2005/0080439 A1* | 4/2005 | Carson et al. | 606/153 |
| 2005/0096722 A1* | 5/2005 | Lootz et al. | 623/1.11 |
| 2005/0107870 A1* | 5/2005 | Wang et al. | 623/1.44 |
| 2005/0187427 A1* | 8/2005 | Connors et al. | 600/29 |
| 2006/0052863 A1* | 3/2006 | Harder et al. | 623/1.38 |
| 2006/0052864 A1* | 3/2006 | Harder et al. | 623/1.38 |
| 2006/0100478 A1* | 5/2006 | Connors et al. | 600/29 |
| 2006/0224183 A1* | 10/2006 | Freudenthal | 606/213 |
| 2007/0010702 A1* | 1/2007 | Wang et al. | 600/8 |
| 2007/0135908 A1* | 6/2007 | Zhao | 623/1.46 |
| 2007/0178221 A1 | 8/2007 | Sims et al. | |
| 2007/0225753 A1* | 9/2007 | Connors et al. | 606/204.25 |
| 2007/0225803 A1* | 9/2007 | Connors et al. | 623/4.1 |
| 2008/0027478 A1* | 1/2008 | Connors et al. | 606/192 |
| 2008/0269789 A1* | 10/2008 | Eli | 606/159 |
| 2008/0269871 A1* | 10/2008 | Eli | 623/1.15 |
| 2008/0286328 A1* | 11/2008 | Schlottig et al. | 424/423 |
| 2008/0311281 A1* | 12/2008 | Andreacchi et al. | 427/2.25 |
| 2008/0318044 A1* | 12/2008 | Tian et al. | 428/401 |
| 2009/0075575 A1* | 3/2009 | Tallberg et al. | 452/21 |
| 2009/0105527 A1* | 4/2009 | Connors et al. | 600/30 |
| 2009/0138070 A1* | 5/2009 | Holzer et al. | 623/1.15 |
| 2010/0009142 A1 | 1/2010 | Quandt et al. | |
| 2010/0049310 A1 | 2/2010 | Quandt et al. | |
| 2010/0057200 A1* | 3/2010 | Flechsenhar et al. | 623/1.46 |
| 2010/0065192 A1* | 3/2010 | Wilson et al. | 156/180 |
| 2010/0065717 A1* | 3/2010 | Wilson et al. | 249/13 |
| 2010/0131050 A1* | 5/2010 | Zhao | 623/1.42 |
| 2010/0241214 A1* | 9/2010 | Holzer et al. | 623/1.15 |
| 2010/0312328 A1* | 12/2010 | Shulze et al. | 623/1.16 |
| 2012/0125888 A1 | 5/2012 | Quandt et al. | |
| 2012/0143318 A1* | 6/2012 | Gulcher | 623/1.46 |
| 2012/0323309 A1* | 12/2012 | Cattaneo | 623/1.24 |
| 2013/0035759 A1* | 2/2013 | Gross et al. | 623/2.38 |
| 2013/0218255 A1* | 8/2013 | Cattaneo et al. | 623/1.11 |
| 2013/0233492 A1* | 9/2013 | Wilson et al. | 156/382 |
| 2013/0243989 A1* | 9/2013 | Ridges et al. | 428/36.91 |
| 2013/0267868 A1* | 10/2013 | Connors et al. | 600/561 |
| 2014/0309725 A1* | 10/2014 | Bar et al. | 623/1.38 |
| 2015/0032197 A1* | 1/2015 | Bar et al. | 623/1.11 |
| 2015/0119971 A1* | 4/2015 | Bar et al. | 623/1.13 |
| 2015/0148588 A1* | 5/2015 | Connors et al. | 600/30 |

FOREIGN PATENT DOCUMENTS

| | | |
|---|---|---|
| DE | 102009023371 | 12/2010 |
| WO | 2004008504 | 1/2004 |
| WO | 2007093423 | 8/2007 |
| WO | 2008022799 | 2/2008 |

* cited by examiner

METHOD FOR PRODUCING A MEDICAL DEVICE

CROSS-REFERENCE TO RELATED APPLICATION

This application is the U.S. national phase of PCT Appln. No. PCT/EP2011/002137 filed on Apr. 28, 2011, which claims priority to German Patent Application No. 10 2010 018 541.8 filed on Apr. 28, 2010, the disclosures of which are incorporated in their entirety by reference herein.

DESCRIPTION

The invention relates to a method for producing a medical device.

For the treatment of vascular lesions, particularly in cerebral vessels, with stents or generally with tubular structures, i.e. three-dimensional structures, it is expedient for the latter to have quite a high degree of flexibility so as to be able to move and position these structures in tightly curved vessels. Lattice-shaped structures are lengthened in the axial direction by curvature, the areas of the structures located on the outside of the curvature expanding or stretching more than the areas arranged closer to the center of the curvature. There is therefore a relationship between the flexibility, in the sense of being able to curve or bend, and the change in length or the maximum lengthening of the lattice-shaped structure.

On account of the small dimensions of the lattice-shaped structures, particularly of the stents, which dimensions are in the lower micrometer range, it is advantageous if the radial force transferred to the vessel wall by the stent or by the lattice-shaped structure is distributed as uniformly as possible, at the same time with the aim of maintaining the flexibility. Moreover, the ease of crimping of the lattice-shaped structure is important for introducing the structure into the body by means of a catheter. Lattice-shaped structures that meet the aforementioned requirements in terms of flexibility, ease of crimping and distribution of radial force can be produced, for example, by applying a cover to the elements of the lattice structures, in particular to the webs, said cover being slightly wider than the width of the webs. This can result in a profile that is T-shaped in cross section and that is composed, firstly, of the web and, secondly, of the cover extending perpendicular to the web.

Other areas of use in which a cover, in particular a structured cover, is applied to a lattice-shaped support structure are known, for example in connection with the production of clot filters, which are used in the treatment of stensoses in order to prevent thrombotic material detaching from the vessel walls and passing into the blood stream.

A production method of this kind is known, for example, from WO 2008/022799 A2. In the known method, a lattice structure is applied to a substrate, and the substrate and the lattice structure are connected by an adhesive such that the openings of the lattice structure are to some extent tightly closed by the substrate. The openings of the lattice structure are filled with a sacrificial material from the uncovered side, such that, after removal of the substrate, a relatively smooth and closed surface is obtained on the side previously connected to the substrate. The cover layer is then deposited on said surface and can be structured after removal of the sacrificial material. In this way, the desired structures can be produced easily and inexpensively.

However, in the production of the lattice structure, variations can arise in the wall thickness or width of the individual elements of the structure, for example of the webs. Moreover, the elements of the structure can have irregular edges, in particular rounded edges, which occur during electropolishing of the elements of the structure. These contours of the lattice elements can impair the application and adherence of the cover to the lattice elements.

The object of the invention is to make available a method for producing a medical device with a lattice structure which is connected at least in some areas to a cover, wherein the connection between the lattice structure and the cover is improved.

According to the invention, this object is achieved by a method having the features of claim 1.

The invention is based on the concept of making available a method for producing a medical device with a lattice structure which is connected at least in some areas to a cover, said method having the following steps:

The lattice structure is arranged on a substrate via the side that is to be connected to the cover. The lattice structure has the side arranged on the substrate pressed at least partially into the substrate. The lattice structure is coated with a first layer of a sacrificial material, such that at least some of the interstices of the lattice structure are covered by the first layer, and the first layer, together with the lattice structure, forms a substantially closed surface on the side to be connected to the cover. This means that the lattice structure is at least partially filled with the sacrificial material of the first layer. The substrate is removed, such that the side of the lattice structure is accessible that is to be connected to the cover. A second layer for forming the cover is applied to the side of the lattice structure previously pressed into the substrate. The sacrificial material is removed.

The medical device obtainable in this way has a supporting lattice structure which is connected at least in some areas to a cover, wherein the connection between the lattice structure and the cover is substantially independent of any variations in the contour of the individual elements of the lattice structure.

In contrast to the method according to WO 2008/022799 A2, in which the lattice structure lies flat on the substrate, the lattice structure in the method according to the invention is actively pressed into the substrate after being applied. This has the effect that the contours of the individual lattice elements of the lattice structure are reproduced in the substrate, such that the substrate covers a part of the lattice elements, namely the critical areas, in particular the edge areas. The lattice elements make complete contact with the substrate on the side to be connected to the cover, such that the formation of shadow areas is avoided. The first layer of the sacrificial material, which fills the interstices or openings of the lattice structure, thus covers the substrate-free part of the lattice elements, i.e. the non-critical areas which, during the production of the lattice elements, are not prone, or are less prone, to variations in contour. In this way, contact between the first layer of the sacrificial material and the lattice structure is as complete as possible.

After the substrate has been detached, the areas of the lattice structure previously covered by the substrate, i.e. the critical areas of the lattice structure, protrude slightly from the first layer of the sacrificial material, specifically according to the depth to which the lattice structure has been pressed into the substrate. Therefore, during the subsequent application of the second layer for forming the cover, the second layer can completely or almost completely cover the protruding areas of the lattice structure regardless of their contour or of any variations in their contour. In this way, the adherence of the cover to the lattice structure is improved in the sense of a permanent and firm connection. The depth of pressing in can be adjusted at least within a range of 30 nm to 200 nm (range for the lower limit), i.e. the lower limit can be at least 30 nm, in particular at least 40 nm, in particular at least 50 nm, in particular at least 75 nm, in particular at least 100 nm, in particular at least 125 nm, in particular at least 150 nm, in particular at least 175 nm, in particular at least 200 nm, in particular at least 225 nm, in particular at least 250 nm, in particular at least 275 nm, in particular at least 300 nm, in particular at least 350 nm, in particular at least 400 nm. In this way, a good adherence of the cover to the lattice elements is achieved, and growth of the second layer, in particular of the copper, under the lattice elements is avoided. The maximum depth of pressing in is adjusted within a range of 0.4 to 2 μm (range for the upper limit), i.e. at most 2 μm, in particular at most 1 μm, in particular at most 0.8 μm, in particular at most 0.6 μm, in particular at most 0.4 μm. This avoids excessive contouring of the cover or film and possible formation of a channel between cover and lattice elements. The total range is ca. 30 nm to 2 μm.

The depth of pressing in or the depth of penetration of the lattice structure into the substrate can be chosen by a person skilled in the art according to the nature of the lattice structure in the area of the edges of the lattice elements. The deeper the lattice structure is pressed into the substrate, the further the extent to which the second layer for forming the cover covers the lateral areas of the lattice elements that are arranged substantially perpendicular to the outer face of the lattice structure which, during use or in the expanded state, bears on the vessel wall and transfers radial forces.

In a preferred embodiment of the method according to the invention, the lattice structure is pressed into the substrate in such a way that edges or lateral roundings of the lattice structure are embedded in the substrate. This means that, after the removal of the substrate, the areas of the lattice structure that are critical for the connection between the lattice structure and the cover can be connected to the second layer for forming the cover.

The ratio between the part of the lattice structure pressed into the substrate and the part of the lattice structure located outside the substrate can be at least 0.0005, in particular at least 0.001, in particular at least 0.005, in particular at least 0.01, in particular at least 0.03, in particular at least 0.05, in particular at least 0.07, in particular at least 0.1, in particular at least 0.15, in particular at least 0.2. The aforementioned ratio between the pressed-in part and free part of the lattice webs can be related, for example, to webs with a web thickness of 30 μm to 60 μm and/or to the aforementioned ranges for the upper and lower limits of the depth of pressing in.

The pressing of the lattice structure into the substrate can be made easier by virtue of the fact that the substrate is flexible and/or has an outer layer of a flexible material, in particular an outer layer of photoresist or a viscous polymer, which outer layer yields when the substrate is pressed into. The outer layer of a photoresist or of the viscous polymer has the advantage that the lattice structure is fixed on the substrate on account of the adhesive properties of the photoresist. Another advantage lies in the etching selectivity, and also in the possibility that a start layer for the galvanic process can be deposited on this outer layer.

In order to remove the substrate, it may be sufficient to remove the outer layer of the substrate, thereby making detachment of the substrate easier.

The coating of the lattice structure with the first layer of a sacrificial material can be improved if the lattice structure, before being coated with the first layer, is coated with a start layer. Preferably, the sacrificial material of the first layer and/or the start layer are formed from a metallic material, in particular from the same metallic material or from different metallic materials.

The coating of the lattice structure with the start layer can be carried out by a gas phase deposition method, in particular a PVD method, in particular by sputtering, and/or the coating of the lattice structure with the first layer of a sacrificial material can be carried out by a galvanic method. Applying the start layer by using a gas phase deposition method has the advantage that the lattice structure can be covered by a thin start layer. The gas phase deposition method permits a uniform coating of the lattice structure and of the substrate, such that the formation of cavities in the subsequent treatment is avoided. In addition, the start layer improves the subsequent complete filling of the lattice structure. For filling the interstices between the individual elements of the lattice structure, a particularly suitable method is a galvanic method in which, within a relatively short period of time, a sufficiently large amount of material is deposited on or in the lattice structure. It is also possible for the first layer of the sacrificial material to be applied completely by the gas phase deposition method, i.e. to fill the interstices or openings of the lattice structure by sputtering.

In another particularly preferred embodiment, the second layer for forming the cover is applied by a gas phase deposition method, in particular a PVD method, in particular by sputtering. In this way, thin layers can be generated for forming the cover (thin-film technology). The second layer for forming the cover can be structured after application, in particular by a lithographic method. In this way, the cover can be adapted to the particular use. For example, by the structuring of the second layer, the individual lattice elements can be given profiles with a T-shaped cross section, such that three-dimensional lattice structures or lattice-shaped structures can be produced that have excellent properties as regards distribution of radial force, ease of crimping, and flexibility.

In another preferred embodiment, before the application of the second layer, a third layer of a sacrificial material is applied to the side of the lattice structure previously pressed into the substrate. This opens up further possibilities for varying the production method and thus producing devices with different properties, for example with areas with or without a cover. The third layer of the sacrificial material can be structured in such a way that the lattice structure is partially covered by the third layer, wherein in particular individual elements of the lattice structure are completely covered and/or not covered and/or partially covered.

The substrate and/or the outer layer can have a three-dimensional structure, in such a way that the three-dimensional structure is transferred to the subsequently applied layers. This opens up further possibilities for varying the properties of the device, in particular the cover of the device.

The second layer can be produced, for example, from bioresorbable materials, in particular from magnesium, and/or from X-ray-visible materials, in particular tantalum.

The second layer can be the sole layer for forming a single-ply cover. Alternatively, the second layer can comprise at least one further subsidiary layer, in particular several subsidiary layers, in order to form a multi-ply cover. In this way, different properties of the cover can be adjusted. For example, an X-ray-visible layer can be provided and/or, in the case of the resorbable materials, layers with different rates of breakdown can be provided. To make matters clear, it will be noted that the subsidiary layers of the second layer belong to the cover and are to be distinguished from the third layer, which forms a temporarily applied layer of sacrificial material for structuring or modifying the cover, i.e. the second layer.

The invention is explained in further detail below on the basis of illustrative embodiments and with reference to the schematic drawings, in which.

The method for producing a medical device is generally suitable for producing planar lattice structures or lattice-shaped structures with a cover. The planar lattice structure with the cover can be shaped, for example cylindrically shaped, to form a three-dimensional medical device. The shaping can be carried out to produce implants, for example stents, or devices that can be temporarily inserted into the body, for example clot catchers or clot filters. The method is suitable for producing lattice structures with T-shaped webs, in particular stents with webs of this kind. The method is also suitable for producing implants, in particular stents with completely covered cells, for example for producing a completely covered stent to arrest vascular bleeding. The method can also be used to produce implants, in particular stents, with covered cells, in which case the covering of the cells has a structuring, in particular a perforation, such that the stent can be used as a flow diverter, for example. The method is also suitable for producing implants, in particular stents, with partially covered cells which have movable flaps, such that the cells can be opened and closed. Moreover, stents with partially covered cells can be produced for aneurysm coverage and/or for plaque coverage, in which case it possible to permit blood flow through perforations and/or blood flow from side vessels and/or a passage for a catheter for the catheterization or coiling of aneurysms.

To produce rotationally symmetrical forms, such as stents, the originally planar structures can be shaped, for example rolled, and connected at their free longitudinal edges, in particular with a form fit, a force fit or an integrally bonded fit, for example by welding, gluing or crimping, preferably with sleeves or similar auxiliaries. Thereafter, the structures can be heat-treated in order to influence the structural properties.

It is also possible, with the aid of the method, to produce planar lattice structures that have a cover and that are used in the planar form.

The method thus affords the possibility of producing planar lattice structures, which are used in the planar form, and also three-dimensional structures, which are formed from a planar initial structure with a cover, for example by cylindrical shaping. Examples of possible three-dimensional structures are stents or other medical devices.

On account of their small thickness, the lattice structures with or without a cover can also be referred to as films.

Various methods can be used to produce the lattice structure 10. For example, it is possible to produce the initial lattice structure 10 by PVD methods, in particular by magnetron sputtering, in which self-supporting structures are formed by the sputtering. An example of the production of the lattice structure 10 by sputtering is shown in FIGS. 11a, 11b and 11c.

A first layer in the form of a web attachment layer 2a, which is structured by an etching process, is applied to a substrate. The structured first layer is undercut by a wet chemical etching process acting on the substrate layer 3. A web constructional layer 2b is then applied to the first layer. In order to form the self-supporting lattice structure, the substrate layer 3 is removed. In the method according to FIGS. 11a to 11c, the web attachment layer 2a has a smaller layer thickness than the web constructional layer 2b. The first layer with the web attachment layer 2a is integrally bonded to the web constructional layer 2b, in such a way that the web attachment layer 2a and the web constructional layer 2b together form the webs of the self-supporting lattice structure. The above-described method for producing a self-supporting sputtered lattice structure is explained in more detail in the application DE 10 2009 023 371, which was unpublished at the filing date of the present invention and belongs to the applicant, and of which the content is incorporated into this application. With this method for producing the supporting lattice structure 10, it is possible to provide very precise and exact edges of the individual elements of the lattice structure.

Figure 1:
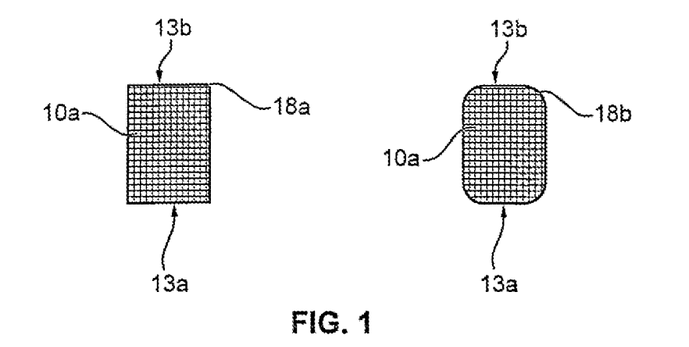
FIG. 1 shows cross sections through two lattice elements with different edges.
Figure 11A:
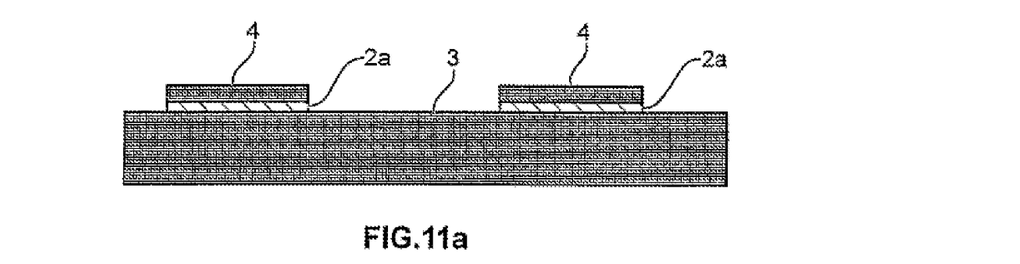
Figure 11B:
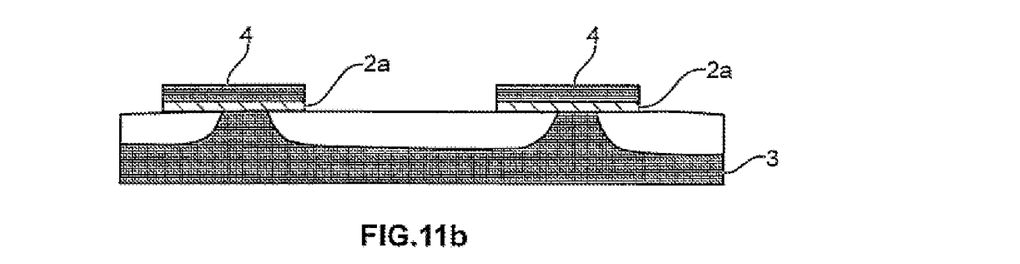
Figure 11C:
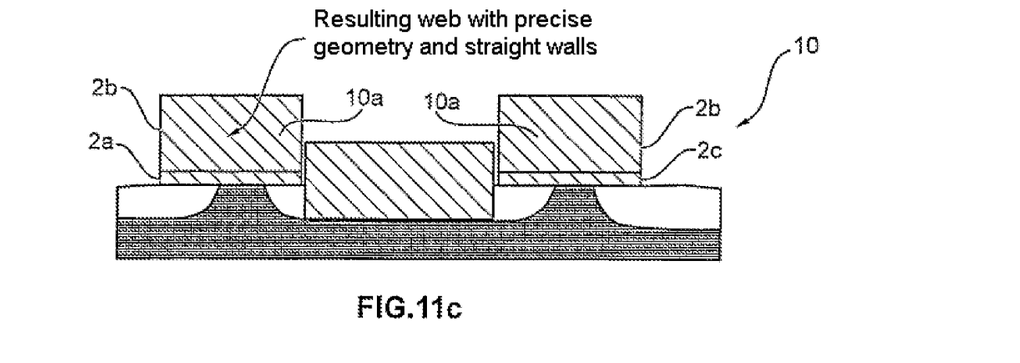

An example of an element of the lattice structure that is produced by the method according to FIGS. 11a to 11c is shown in FIG. 1. It will be seen from the latter that the element 10a (shown in cross section) of the lattice structure 10, for example a web of the lattice structure 10, has schematically indicated sharp edges 18a without any rounding (left-hand view in FIG. 1). In the right-hand view in FIG. 1, the cross section of an element 10a of a lattice structure 10 is shown which is produced, for example, by laser cutting and has edges 18b or roundings that have been made round by electro-polishing. As has been explained in the introduction, these roundings 18b pose a problem when connecting the element 10a to the cover. The method is not only suitable for connecting the element 10a with rounded edges according to the right-hand view to the cover, but also for connecting the element 10a according to the left-hand view in FIG. 1.

A first side 13a of the lattice structure 10 or of the element 10a is to be connected to a cover. The opposite, second side 13b of the lattice structure 10 remains free of any cover. It is also possible to provide the second side with a cover too, for example by a conventional method or by the method according to the invention or the method disclosed in the illustrative embodiments, or to otherwise modify it. The accessibility of the second side for application of the cover by the method according to the invention can be obtained, for example, in structured partial areas and/or cover-free partial areas.

Generally speaking, the lattice structure of the device can be produced in any desired manner, for example by magnetron sputtering or by laser cutting, etching processes, micromilling, LIGA methods or other processes suitable for producing lattice structures.

The step of producing the supporting lattice structure can be part of the overall production method. It is also possible for first step of producing the lattice structure to be carried out separately in another method and, accordingly, for prefabricated lattice structures to be connected to a cover by the method according to this application.

The lattice structure can be configured in various shapes, the lattice structure having cells (not shown). The lattice structure can have open or closed cells. The individual elements of the lattice structure can include webs, connectors, tips, or other elements of the lattice structure. The profile of the webs is not completely rectilinear. The profile can be curved or barrel-shaped.

The lattice structure forms the bearing support structure of the device. In the case of an implant, in particular a stent, it applies the radial force that acts on the vessel wall. The lattice structure can be self-expanding or can expand by application of external forces (balloon dilatation). The materials used for producing the lattice structure depend on the specific use that is envisioned and include the materials customarily used to produce implants or other medical devices that can be inserted temporarily into the body, for example biocompatible shape-memory materials, in particular NiTi alloys such as Nitinol, or bioresorbable materials such as iron alloys or magnesium or tantalum, or in each case alloys thereof, or other materials.

Figure 2:
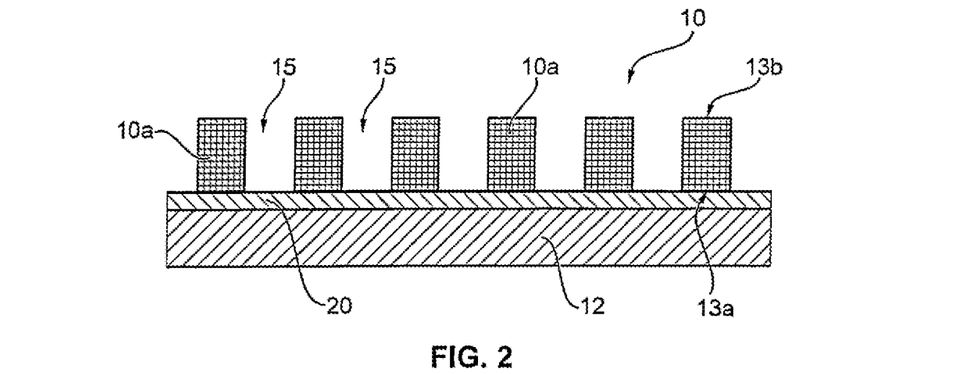
FIG. 2 shows the first step of applying the lattice structure to the substrate.

FIG. 2 shows that, in the first work step, the lattice structure 10 is arranged on a substrate 12. The substrate 12 is flexible. This can be achieved, for example, by the entire substrate being made of a flexible material. As in the example shown, the substrate can comprise a flexible outer layer 20, on which the lattice structure 10 is arranged. The outer layer 20 can be a photoresist, for example. In this case, the substrate 12 can comprise a hard supporting portion, on which the outer layer 20 is applied. The outer layer 20 is advantageously plastically deformable.

On account of the low inherent weight of the lattice structure 10 or film, no change of any kind occurs in the shape of the substrate 12 or of the outer layer 20 in the first work step. In addition, the nature of the process means that the lattice structure 10 or film is slightly curved, with the result that areas of the lattice structure 10 do not touch the substrate 12. The lattice structure 10 cannot be pressed in without the action of an external force.

The lattice structure 10 is positioned on the substrate 12, in particular on the photoresist 20, via a first side 13a or the side 13a to be connected to the cover. By virtue of its adhesion properties, the photoresist has the effect that the lattice structure 10 is sufficiently well fixed on the substrate. The interstices 15 between the individual lattice elements 10a, or the openings of the lattice structure 10, extend substantially perpendicularly with respect to the surface of the substrate 12. The substrate 12 is accessible by way of the interstices 15.

It will be noted at this point that the term substrate comprises both the supporting part and also the flexible part on which the lattice structure 10 is arranged. It is possible to produce the substrate entirely from a flexible material that is sufficiently plastically deformable, so as to allow the lattice structure to be pressed in. The substrate can thus be constructed in one part or two parts, in particular in multiple parts or multiple layers.

Figure 3:
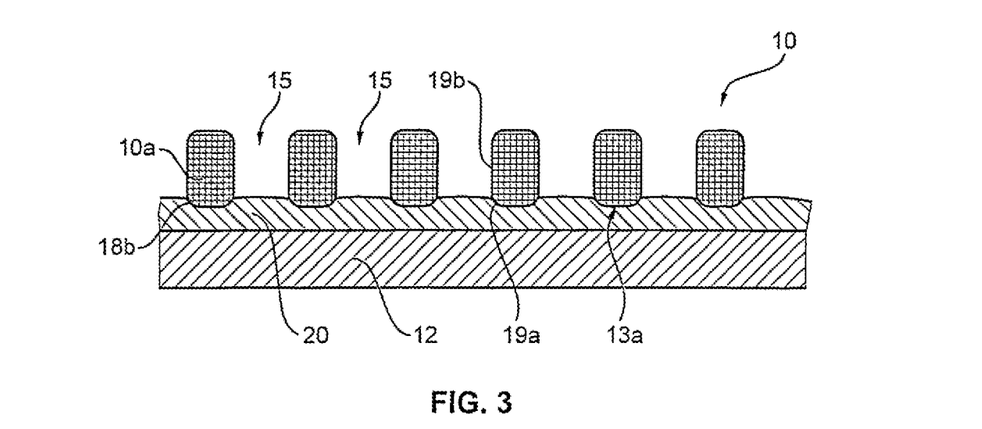
FIG. 3 shows the second step of pressing the lattice structure into the substrate.

FIGS. 2 and 3 show lattice elements 10a with precise edges (FIG. 2) and lattice elements 10a with rounded edges (FIG. 3). The method is suitable in both cases for connecting the cover to the lattice structure 10.

In the second step according to FIG. 3, the lattice structure 10 is pressed into the substrate 12, in particular into the outer layer 20 of the substrate 12, specifically by being pressed in actively, i.e. by the action of an external force. To do so, an external force that acts substantially perpendicularly with respect to the substrate is applied to the lattice structure 10. The external force is so great that the lattice structure 10 is pressed into the substrate 12 or the outer layer 20 at least in the area of the edges 18a or of the roundings 18b on the first side 13a of the lattice structure. The depth to which it is pressed in can be varied within the limits mentioned in the introduction and may optionally exceed or fall short of these limits. The force needed to press it in is determined by a person skilled in the art, for example by experimentation. The pressure needed to press it in depends on the surface. The force can, for example, be from 0.5 to 5 N.

The lattice structure 10 is pressed in across the whole surface area. In addition, the lattice structure 10 is pressed in homogeneously, with the result that the depth to which it is pressed in is as uniform as possible across the surface extent of the lattice structure 10. When the force for pressing it in is applied, the lattice structure 10 lies flat on the substrate 12, such that all elements 11 of the lattice structure 10, or substantially all of the elements 11 of the lattice structure 10, touch the substrate. The external pressure acting on the lattice structure 10 has the effect that the surface of the substrate 12 or of the outer layer 20 undergoes deformation, in particular plastic deformation. A profile is thereby formed in the surface that corresponds to the lattice structure 10, in particular to the arrangement of the elements 11 of the lattice structure 10. The elements thus penetrate into the original plane surface of the substrate 12 or of the outer layer 20 and form depressions in the surface of the substrate 12 or of the outer layer 20, in which depressions the elements 11 are partially arranged or received. As regards the numerical values of the depth of pressing in, which depth corresponds to the dimension of the depressions, reference is made to the aforementioned ranges, including the stated numerical values or limits.

To ensure that the lattice structure 10 is pressed in homogeneously across the whole surface area, a plate with a high-precision surface is provided which is arranged on the side 13b of the lattice structure 10 facing away from the substrate 10 and which is pressed onto the lattice structure 10 by the action of an external force. For this purpose, adjusting means known per se are provided that permit adjustment lengths in the required nm range or μm range. To measure the depth of pressing in, it is possible, for example, to use a profilometer, which is known per se and which runs along the profile of the lattice structure 10 and of the substrate 12 with nanometer precision.

As is shown in FIG. 3, the lattice structure 10 is pressed partially into the outer layer 20. The depth of penetration shown in FIG. 3, or the depth to which the lattice structure 10 is pressed into the substrate 12, is given by way of example. It is also possible to press the lattice structure 10 more strongly into the outer layer, for example in order to achieve a greater degree of coverage of the edge areas of the lattice structure 10. The lattice structure 10 is pressed so deeply into the substrate 12 or the outer layer 20 that the edges 18a or the roundings 18b at least partially disappear in the outer layer 20 or in the substrate and are embedded therein. This has the effect that the elements 10a, in the area of the edges, are touched or covered substantially completely by the substrate 12 or the outer layer 20, even if the wall thickness of the elements 10a varies.

Figure 4:
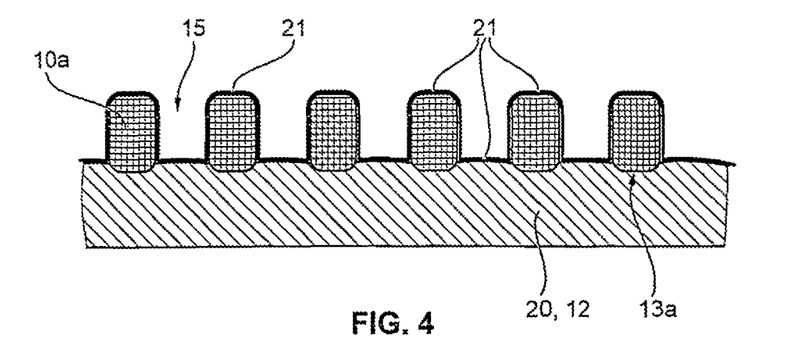
FIG. 4 shows the third step of coating the lattice structure with a start layer.

In the third work step according to FIG. 4, an intermediate material or start layer 21 is applied to the lattice structure 10 and to the substrate 12 or the outer layer 20. As can be seen from FIG. 4, by coating the lattice structure 10 with the start layer 21, the substrate 12 or the outer layer 20 is also coated, specifically in the area of the interstices 15, such that there is a complete coverage or at least a substantially complete coverage of the individual lattice elements 10a, except for the area of the lattice elements 10a that is embedded in or pressed into the substrate 12 or the outer layer 20. By means of the complete contact of the elements 10a or webs or by means of the elements 10a or webs being pressed into the substrate 12, shadow areas in which the intermediate material would have no contact with the elements 10a or webs are avoided.

An example of a suitable material for the start layer 21 is copper, which is sputtered onto the lattice structure 10a.

In FIG. 4, the distinction between outer layer 20 and supporting substrate 12 is not shown. Like the other figures, FIG. 4 is to be understood in the sense that the lattice structure 10 is pressed either into the outer layer 20, for example the photoresist, or into the supporting structure of the substrate, each of them plastically deforming.

Figure 5:
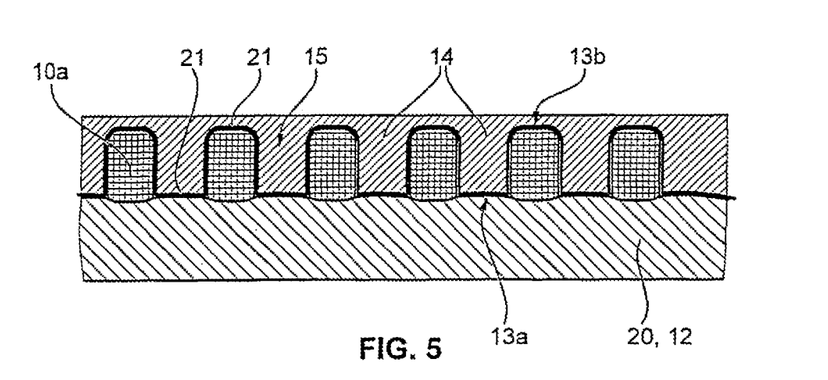
FIG. 5 shows the fourth step of coating the lattice structure with the first layer of a sacrificial material.
Figure 6:
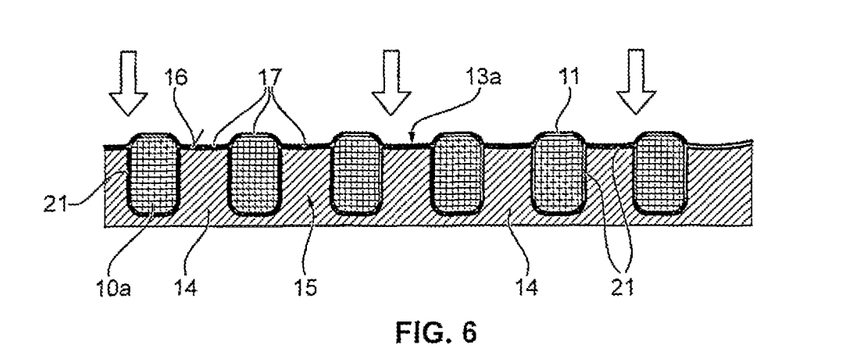
FIG. 6 shows the fifth step of coating the lattice structure with a second layer for forming the cover, after the substrate is removed.

In the fourth work step according to FIG. 5, it will be seen that the interstices 15 or openings of the lattice structure 10 are filled by a first layer 14 of a sacrificial material. The interstices 15 are preferably filled completely with the first layer 14 of the sacrificial material, such that a stable and easy-to-handle unit composed of lattice structure 10 and first layer 14 is obtained overall. The first layer 14 preferably covers the second side 13b facing away from the first side 13a of the lattice structure, such that a particularly firm and durable contact is achieved between the fist layer 14 and the lattice structure 10. It is also possible for the interstices 15 to be filled only partially, for example to only half the height of the elements 10a. It is sufficient that the interstices 15 of the lattice structure 10 are covered with the first layer 14 such that the lattice structure 10, together with the first layer 14, forms, on the first side 13a to be connected to the cover, a substantially closed surface 16 after the substrate is removed (FIG. 6). The closed surface 16 forms a substantially continuous contact face for the second layer 17 that is subsequently to be deposited in order to form the cover 11 (FIG. 6).

The first layer 14 of the sacrificial material is applied by a galvanic process. Advantageously, the first layer 14 for filling the interstices 15 is produced from the same material as the start layer 21. It is also possible to fill only partial areas of the lattice structure with the sacrificial layer.

In the fifth work step according to FIG. 6, the cover of the structure is formed. To do so, a film or a second layer 17 for forming the cover is applied by a thin-film method to the side 13a of the lattice structure 10 previously pressed into the substrate 12 or the outer layer 20, after the substrate 12, including the outer layer 20, has been removed (FIG. 6). The second layer 17 can be applied by a PVD method, in particular by magnetron sputtering or another method. As can be clearly seen in FIG. 6, the second layer 17 covers those areas of the elements 10a of the lattice structure 10 that protrude from the first layer 14 of the sacrificial material. Specifically, the areas of the elements 10 that were pressed beforehand into the substrate 12 or the outer layer 20, i.e. the critical edge areas of the elements 10 that are exposed after removal of the substrate 12 or of the outer layer 20, are covered by the layer 17. This ensures particularly good adherence of the layer 17, or generally of the film, to the elements 10, 10a or to the webs. The application of the second layer 17 to the side 13a of the lattice structure 10 previously covered by the substrate 12 is indicated in FIG. 6 by three arrows extending at right angles to the lattice structure 10.

Figure 7:
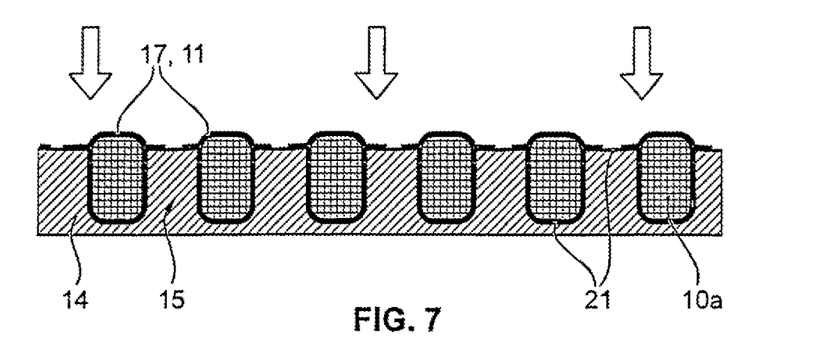
FIG. 7 shows the sixth step of structuring the second layer for forming the cover.

In the sixth work step according to FIG. 7, the continuous layer 17 or film is structured, for example by a lithographic method known per se. The shape of the cover is thereby produced, for example, as is shown in FIG. 7, the T-shaped cross section that forms in conjunction with the elements 10a.

Figure 8:
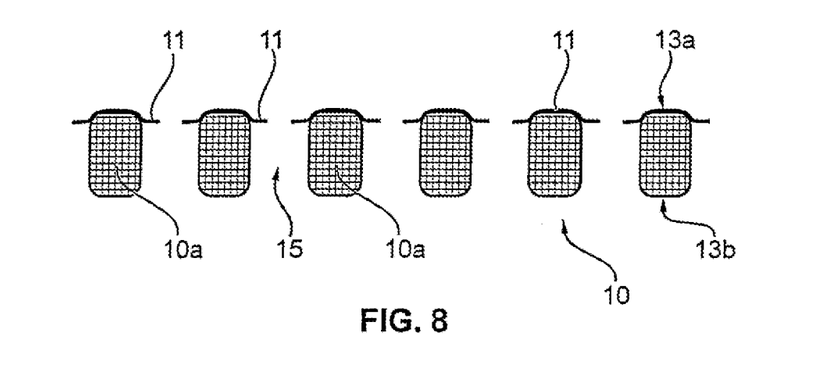
FIG. 8 shows the seventh step of removing the sacrificial material.

In the seventh work step according to FIG. 8, the first layer 14 of the sacrificial material, including any start layers 21, is removed, for example by etching. Thus, the elements 10a or the lattice structure 10 with the cover 11 remain as an end product, or possibly also as an intermediate product that undergoes further treatment. For example, the lattice structure 10 with the cover 11 can be subjected to heat treatment such that in the case of shape-memory layers, for example of NiTi alloys, the structure can be adjusted to a transition temperature. In this way, three-dimensional forms of the lattice structure, for example cylindrical forms (stents), can also be fixed.

Using the method, the lattice structure 10 and the cover 11 can be produced from the same material, for example from a shape-memory material. Other materials, for example bioresorbable materials such as magnesium or iron, are likewise possible. It is also possible, using the method, to combine different materials for the lattice structure 10 and the cover 11. For example, the skeleton or the lattice structure can be produced from a shape-memory material, for example from a NiTi alloy, and the surrounding layer or the cover 11 can be produced from iron. Moreover, it is also possible for the cover 11, or generally the enclosing outer layer, to be produced from a bioresorbable material, for example from polymers. It is also possible, conversely, to produce the lattice structure 10 from a bioresorbable material and the cover 11 from a resistant material.

Figure 9:
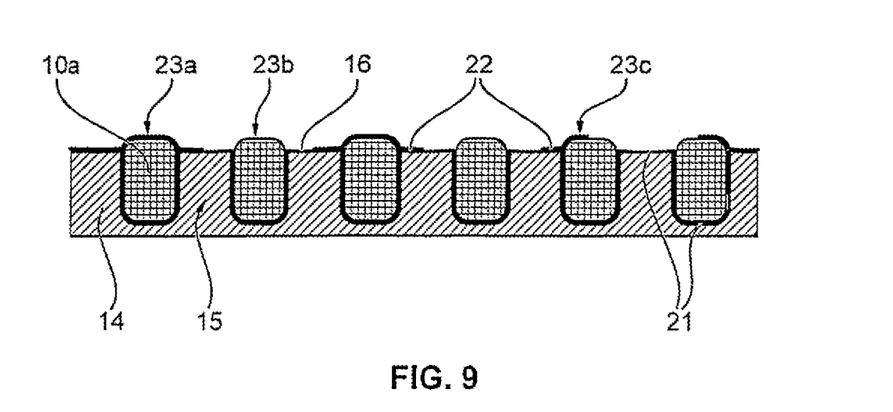
FIG. 9 shows a further illustrative embodiment of the method, in which a third layer is applied before the application of the second layer.
Figure 10:
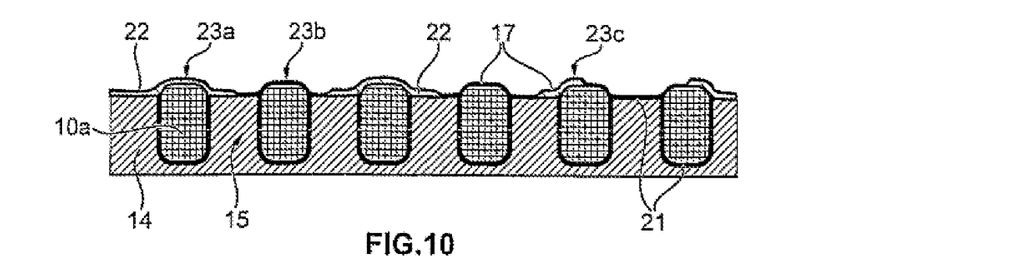
FIG. 10 shows the step of applying the second layer to the material that has been pre-treated according to FIG. 9, FIGS. 11a to 11c show an example of a method for producing the supporting lattice structure.

FIGS. 9 and 10 show an alternative or development of the method according to FIGS. 2 to 8. The work steps according to FIGS. 2 to 5, including the step of removing the substrate 12, can precede the work step according to FIG. 9.

After the substrate 12 or the outer layer 20 has been removed, or generally after the side 13a of the lattice structure 10 to be connected to the cover 11 has been exposed, a third layer 22 of a sacrificial material is applied to the first side 13a. The third layer 22 can be structured. The structuring can be done in such a way that the elements 10a remain only party covered (see partial coverage 23c). It is also possible to completely cover the elements 10a (see complete coverage 23a) or to leave some elements 10a exposed (see without coverage 23b). The aforementioned structuring possibilities can be combined in any desired manner.

In the subsequent work step according to FIG. 10, the second layer 17 for forming the cover is applied. To make matters clear, it will be noted that the third layer 22 is applied as a sacrificial layer at a time before the second layer 17 is applied. Because of the partial coverage 23c or the complete coverage 23a, there is no connection between the second layer 17 and the surface of the elements 10a in the covered areas. The connection between the second layer 17 and the surface of the elements 10a occurs only in the uncovered areas, i.e. in the completely uncovered areas 23b or in the partially uncovered areas 23c. As a result of the partial connection of the film or layer 17 or cover 11, a modification of the cover 11 is achieved. For example, the cover and the lattice structure can be arranged so as to move relative to each other in some areas. The cover can be designed in the form of flaps. As a result of the relative movement between cover and lattice structure, increased flexibility is achieved during crimping.

The third layer 22 of the sacrificial material is removed prior to the final production of the device.

In a further illustrative embodiment, the substrate 12 and/or the outer layer 20 can have a three-dimensional structure. For example, grooves and/or protuberances can be formed in the surface of the substrate 12 or of the outer layer 20. During the subsequent sputtering-on of the second layer 17 for forming the cover 11, the three-dimensional structure of the substrate 12 or of the outer layer 20 is transferred to the second layer 17 or the cover 11. This has the advantage that three-dimensional structures can be constructed, for example in order to optimize the flow conditions and/or the endothelialization. Alternatively or in addition, fold lines can be formed in the cover 11, which make the overall system easier to crimp for insertion into a catheter or generally into a delivery system.

In another preferred illustrative embodiment, bioresorbable materials, for example magnesium or iron, and/or X-ray-visible materials, for example tantalum, can be applied in order to form the cover 11. It is then possible that the cover 11 is present in a multiply configuration and has several layers of different materials. Alternatively, it is also possible to produce the cover 11 from a single layer, or in a single ply from a plurality of subsidiary layers of the same material. The layer can be composed of a bioresorbable or an X-ray-visible material.

Applying the second layer 17, or generally the layer for forming the cover 11, by a thin-film method, in particular by sputtering or magnetron sputtering, has the advantage that a very thin film can be applied, which in particular is thinner than the prefabricated film connected to the supporting structure by conventional methods. The connection of very thin films by conventional methods often leads to handling problems during the production process. Moreover, connection errors that compromise the stability of the entire structure can arise. In the conventional welding of thin films, the energy needed for the welding has to be precisely regulated. However, the danger of material burning is very high. Adhesion of very thin structures leads to capillary effects, which result in the adhesive migrating into undesired areas of the structure.

By contrast, producing the cover 11 by a thin-film technique, in particular by sputtering, has the advantage that the cover 11 is connected to the lattice structure 10 in situ during production. In this way, very thin films can be applied to the lattice structure 10, without incurring major handling problems during production. These thin films are easier to crimp for insertion into a catheter.

LIST OF REFERENCE SIGNS 10 lattice structure
10a elements of the lattice structure
11 cover
12 substrate
13a first side
13b second side
14 first layer
15 interstices
16 surface
17 second layer
18a edges
18b roundings
19a first part
19b second part
20 outer layer/photoresist
21 start layer
22 third layer
23a complete coverage
23b without coverage
23c partial coverage

The invention claimed is:

1. A method for producing a medical device with a lattice structure which is connected at least in some areas to a cover, in which method comprising the lattice structure is arranged on a substrate via the side that is to be connected to the cover;

the lattice structure has the side arranged on the substrate pressed at least partially into the substrate;

the lattice structure is coated with a first layer of a sacrificial material, such that at least some of the interstices of the lattice structure are covered by the first layer, and the first layer, together with the lattice structure, forms a substantially closed surface on the side to be connected to the cover;

the substrate is removed, such that the side of the lattice structure is accessible that is to be connected to the cover;

a second layer for forming the cover is applied to the side of the lattice structure previously pressed into the substrate; and the sacrificial material is removed.

2. The method as claimed in claim 1, wherein the lattice structure is pressed into the substrate in such a way that edges or lateral roundings of the lattice structure are embedded in the substrate.

3. The method as claimed in claim 1, wherein the ratio between the part of the lattice structure pressed into the substrate and the part of the lattice structure located outside the substrate is at least 0.0005, in particular at least 0.001, in particular at least 0.005, in particular at least 0.01, in particular at least 0.03, in particular at least 0.05, in particular at least 0.07, in particular at least 0.1, in particular at least 0.15, in particular at least 0.2.

4. The method as claimed in claim 1, wherein the substrate is flexible and/or has an outer layer of a flexible material, in particular an outer layer of photoresist or a viscous polymer, which outer layer yields when the substrate is pressed into.

5. The method as claimed in claim 4, wherein, in order to remove the substrate from the lattice structure, the outer layer of the substrate is removed.

6. The method as claimed in claim 1, wherein the lattice structure, before being coated with the first layer of a sacrificial material, is coated with a start layer.

7. The method as claimed in claim 1, wherein the sacrificial material of the first layer and/or the start layer are formed from a metallic material, in particular from the same metallic material or from different metallic materials.

8. The method as claimed in claim 1, wherein the coating of the lattice structure with the start layer is carried out by a gas phase deposition method, in particular a PVD method, in particular by sputtering, and/or the coating of the lattice structure with the first layer of a sacrificial material is carried out by a galvanic method.

9. The method as claimed in claim 1, wherein, during the coating of the lattice structure with the first layer of a sacrificial material, the lattice structure is partially or completely embedded in the sacrificial material.

10. The method as claimed in claim 1, wherein the second layer for forming the cover is applied by a gas phase deposition method, in particular a PVD method, in particular by sputtering.

11. The method as claimed in claim 1, wherein the second layer for forming the cover is structured after application, in particular by a lithographic method.

12. The method as claimed in claim 1, wherein, before the application of the second layer, a third layer of a sacrificial material is applied to the side of the lattice structure previously pressed into the substrate.

13. The method as claimed in claim 12, wherein the third layer of a sacrificial material is structured in such a way that the lattice structure is partially covered by the third layer, wherein in particular individual elements of the lattice structure are completely covered and/or not covered and/or partially covered.

14. The method as claimed in claim 1, wherein the substrate and/or the outer layer have a three-dimensional structure, in such a way that the structure is transferred to the subsequently applied layers.

15. The method as claimed in claim 1, wherein the second layer is applied using bioresorbable materials, in particular magnesium, and/or X-ray-visible materials, in particular tantalum, or in each case alloys thereof.

16. The method as claimed in claim 1, wherein the second layer is the sole layer for forming a single-ply cover, or at least one further layer, in particular several layers, are applied to the second layer in order to form a multi-ply cover.

* * * * *